United States Patent [19]

Syed

[11] Patent Number: 5,470,898
[45] Date of Patent: Nov. 28, 1995

[54] SORBITOL DERIVATIVES AS NUCLEATORS AND CLARIFIERS FOR POLYOLEFINS, AND POLYOLEFIN COMPOSITIONS OBTAINED THEREWITH

[75] Inventor: Abuzar Syed, New Castle County, Del.

[73] Assignee: Montell North America Inc., Wilmington, Del.

[21] Appl. No.: 239,230

[22] Filed: May 13, 1994

Related U.S. Application Data

[63] Continuation-in-part of Ser. No. 85,717, Jun. 30, 1993, abandoned.

[51] Int. Cl.$^6$ ........................................ C08K 5/15
[52] U.S. Cl. ........................................ 524/84; 524/108
[58] Field of Search ........................................ 524/84, 108

[56] References Cited

U.S. PATENT DOCUMENTS

| | | | |
|---|---|---|---|
| 3,721,682 | 3/1973 | Murai et al. | 549/364 |
| 4,131,612 | 12/1978 | Uchiyama | 549/364 |
| 4,267,110 | 5/1981 | Uchiyama | 549/364 |
| 4,314,039 | 2/1982 | Kawai et al. | 525/1 |
| 4,371,645 | 2/1983 | Mahaffey, Jr. | 524/108 |
| 4,483,952 | 11/1984 | Uchiyama | 524/108 |
| 4,808,650 | 2/1989 | Titus et al. | 524/108 |
| 4,845,137 | 7/1989 | Williams et al. | 524/108 |
| 4,902,807 | 2/1990 | Kobayashi et al. | 549/364 |
| 4,996,334 | 2/1991 | Kaitoh et al. | 549/364 |
| 5,216,051 | 6/1993 | Smith et al. | 524/108 |

*Primary Examiner*—Kriellion S. Morgan

[57] ABSTRACT

Disclosed are certain 1,3-2,4-di(substituted arylidene)- and 1,3-2,4-di(substituted heteroarylidene)-D-sorbitols which are useful as clarifying and nucleating additives for crystalline and semi-crystalline polyolefin compositions. Also disclosed are such poly($C_1$–$C_8$ alpha olefin) compositions containing them.

7 Claims, No Drawings

SORBITOL DERIVATIVES AS NUCLEATORS AND CLARIFIERS FOR POLYOLEFINS, AND POLYOLEFIN COMPOSITIONS OBTAINED THEREWITH

CROSS-REFERENCE TO RELATED APPLICATION

The application is a continuation-in-part of the U.S. application, Ser. No. 08/085,717, filed Jun. 30, 1993, now abandoned.

BACKGROUND OF THE INVENTION

This invention relates to sorbitol derivatives useful as nucleators and clarifiers in polyolefin resin compositions and to polyolefin resin compositions in which such derivatives are included, thus imparting improved transparency and improved crystallization response.

Polyolefins such as polyethylene and polypropylene have found extensive use as packaging materials and containers in the form of films, sheets or hollow articles. However, since polyolefins tend to have poor transparency, they cannot fully meet the demand for packaging materials or containers which permit their contents to be viewed from the outside.

It is generally known to use nucleators and clarifiers to reduce product molding cycle times by allowing the polyolefins to which they are added to be crystallized at higher temperatures during injection and blow molding operations. Polyolefins containing such additives require less time in the mold for cooling and the finished product has smaller crystals, resulting in decreased light scattering and improved clarity.

The preparation and purification of dibenzylidene sorbitol is disclosed in U.S. Pat. No. 3,721,682, U.S. Pat. No. 4,131,612 and U.S. Pat. No. 4,267,110; these references also disclose uses which include gelling of organic liquids and clarifying polyolefin resins. Dibenzylidene sorbitol has been proposed as an additive (Japanese Patent Application No. 94424/1974) to improve transparency, but this additive had reported compatibility limitations with polyolefin resins. The addition of a small amount of tribenzylidene sorbitol to dibenzylidene sorbitol improved compatibility with polyolefin resins (U.S. Pat. No. 4,267,110), but it was later reported that it tended slightly to bleed out onto the surface of the resulting molded article, and therefore the surface of the molded article tended to collect static charges and become contaminated.

Polypropylene compositions having improved transparency and being substantially free from bleeding were reported in U.S. Pat. No. 4,314,039 based on the use of 1,3-2,4-di(alkylbenzylidene) sorbitol in which each alkyl group has (the same) 2 to 18 carbon atoms; the position of the alkyl group was reported not to be critical.

There are several commercial nucleators based on sorbitol which are useful in polyolefins including: 1,3-2,4-di(benzylidene)-D-sorbitol (Millad 3905, Milliken Chemical Co.); 1,3-2,4-di-(4-tolylidene)-D-sorbitol (Millad 3940, Milliken Chemical Co.); 1,3-2,4-di-(4-ethylbenzylidene)-D-sorbitol (NC-4, Mitsui Petrochemical Industries, Ltd.).

Processes for preparing dibenzylidene sorbitol and xylitol derivatives are described in U.S. Pat. No. 4,429,140 and U.S. Pat. No. 4,562,265. The substituted benzaldehydes disclosed as useful in the processes for reaction with sorbitol or xylitol include lower alkyl or alkoxy, halogen or nitro group as well as other aromatic aldehydes.

U.S. Pat. No. 4,371,645 discloses various dibenzylidene sorbitol derivatives for use in polyolefin plastic compositions to improve transparency. However, it is taught that the derivatives must be disubstituted with chlorine or bromine. The presence of the halogen is said to significantly improve transparency.

Polyolefin resin compositions employing a variety of dibenzylidene sorbitol derivatives for improved transparency are disclosed in U.S. Pat. No. 4,483,952. The polyolefins include polyethylene and polypropylene as well as copolymers of propylene with a small amount of ethylene. The two substituting groups on the dibenzylidene sorbitol are disclosed as different from each other and in the case where they are alkyl groups, they are limited to three carbon atoms or less. The classes of derivatives are said to have very good compatibility with polyolefin resins, thereby avoiding bleeding out or static charge build-up on the surface of articles molded from the composition.

Another reference which discloses disubstitution by a halogen, in this instance fluorine, is U.S. Pat. No. 4,808,650. The fluorine must be present in the structure in the meta position, although additional fluorine can be present in the para position thus resulting in a tetrafluoro derivative. The latter is said to be particularly effective at concentrations of 0.4 to 0.6% by weight.

Polyolefin compositions with both high clarity and resistance to oxidative degradation are disclosed in U.S. Pat. No. 4,845,137. The improvement is said to result from the presence of a sulfur-containing substituent on at least one of the two benzylidene rings of the dibenzylidene sorbitol. The preferred additive contains a lower alkyl thio group on each ring.

Another process patent, U.S. Pat. No. 4,902,807 discloses a process for batchwise production of substituted or unsubstituted dibenzylidene sorbitol or xylitol based on slowly feeding the primary reactants (polyhydric alcohol and benzaldehyde compound(s)) to the reactor. The primary reactants, and the benzaldehyde compound in particular (col. 3, lines 34–45), are not different from those disclosed in the above references. Various process benefits are attributed to the reaction control features.

U.S. Pat. No. 4,996,334 discloses dibenzylidenesorbitol derivatives having at least one nuclear substituent selected from an ester group such as —COOR$^1$ and an amido group represented by —CONR$_2$R$^3$; R$^1$,R$^2$ and R$^3$ are defined elements or groups. The derivatives are disclosed as useful for heightening transparency and rigidity of resins (col. 1, lines 9–11) although no evidence is provided. The reference disclosure and examples are devoted exclusively to the use of the disclosed compounds as gelatinizers for oils, organic solvents and other fluids.

Dibenzylidenesorbitol derivatives are disclosed in U.S. Pat. No. 5,001,176 for use in combination with a cyclodextrin compound to produce crystalline polyolefin articles with improved transparency and improved odor. The reference does not suggest that the dibenzylidenesorbitol derivatives exemplified in column 3 are novel; it is the use of the cyclodextrin to reduce the odor of the composition, which appears to be the advance.

Mixtures of various dibenzylidene sorbitol and xylitol derivatives useful as nucleating agents for crystalline resin compositions are disclosed in U.S. Pat. No. 5,015,684. The mixtures include dibenzylidene sorbitol and xylitol per se as well as derivatives wherein the rings are substituted with 2 or 3 methyl groups (columns 3 and 4).

More highly substituted benzylidene sorbitols containing $C_1$–$C_4$ dialkyl (or up to a 5 carbon atom carbocyclic ring) substitution on each benzylidene group are disclosed in U.S. Pat. No. 5,049,605. Polymeric compositions containing the additives are said to have improved taste and odor properties.

U.S. Pat. No. 5,023,354 describes an improved process for preparing high purity diacetals in the absence of organic solvents and in an aqueous medium. The advance appears to be the process conditions which are particularly specified; the use of the resulting product for clarifying and stabilizing polyolefins is mentioned in passing (abstract and col. 2, lines 4–8), and it is not suggested that the specific derivatives are novel.

U.S. Pat. No. 5,041,310 discloses a process for coating individual semi-crystalline polymer particles with liquid additive compositions including polyolefin clarifiers, such as sorbitol derivatives which derivatives also function as gelling agents. Several gelling agents are disclosed at col. 3, lines 47–62 including the ring substituted derivatives 4,4'-dimethyl dibenzylidene sorbitol and 4,4'-bis(methylthio) dibenzylidene sorbitol.

While relevant art is available, it is apparent that structural variations lead to differing results; no underlying theory is available which allows for predictability of individual compound performance.

SUMMARY OF THE INVENTION

New and useful compounds have been synthesized which have the ability to function as clarifiers and nucleators in crystalline and semi-crystalline polyolefin compositions, particularly propylene polymer compositions and as nucleators in heterophasic polyolefin compositions.

These compounds are 1,3–2,4-di(arylidene/heteroarylidene)-D-sorbitol derivatives of the following formula:

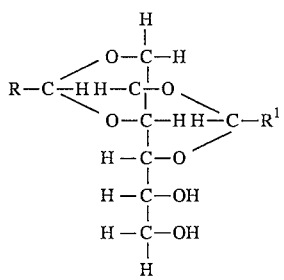

wherein:

(a) R and $R^1$ are the same and represent a member selected from the group consisting of

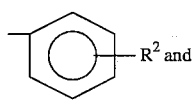

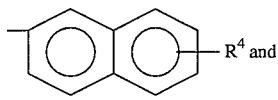

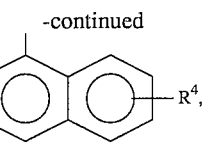

wherein $R^2$ is mono-, di- or tri-substituted on the ring and represents a member selected from the class consisting of $NO_2$ and CN; and wherein $R^4$ is mono-, di-, or tri-substituted on the ring and represents a member selected from the class consisting of $C_1$–$C_6$ alkyl or O-alkyl, and $NO_2$; or (b) R and $R^1$ are different and one of R and $R^1$ is

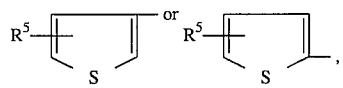

wherein $R^5$ represents a member selected from the class consisting of H, $C_1$–$C_6$ alkyl, $NO_2$, Cl, Br and F, and the other of R and $R^1$ is

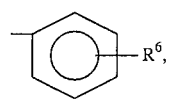

wherein $R^6$ is mono-, di-, or tri-substituted on the ring and represents a member selected from the class consisting of alkyl or O-alkyl groups having 1 to 8 carbon atoms, $NO_2$, CN and COOY, wherein Y is an alkyl having 1 to 8 carbon atoms; or (c) R and $R^1$ are different and R is

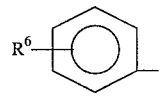

wherein $R^6$ is as defined above, and $R^1$ is

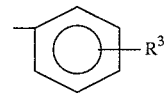

wherein $R^3$ is mono-, di-, or tri-substituted on the ring and represents an alkyl group having 4 to 6 carbon atoms.

In addition, improved polyolefin compositions have been found that consist essentially of at least one homopolymer or copolymer of a $C_2$ to $C_8$ alpha-monoolefin and about 0.05 to about 2.5% by weight, based on the weight of said composition, of a 1,3,-2,4-di(arylidene/heteroarylidene)-D-sorbitol derivative of the above formula.

DETAILED DESCRIPTION

All percentages and parts in this specification are by weight unless stated otherwise.

The new clarifying and nucleating additives of the present invention (sometimes referred to hereinafter as "sorbitol derivatives") are useful in compositions based on crystalline and semi-crystalline polyolefin polymers or polyolefin resin compositions consisting essentially of at least one homopolymer or copolymer of a $C_2$–$C_8$ alpha-monoolefin, particularly propylene polymer material and mixtures of such polyolefin polymers.

The synthetic polymer resin formed by the polymerization of propylene as the sole monomer is called polypropylene. The well-known crystalline polypropylene of commerce is a normally solid, predominantly isotactic, semi-crystalline, thermoplastic homopolymer formed by the polymerization of propylene by Ziegler-Natta catalysis. In such catalytic polymerization the catalyst is formed by an organic compound of a metal of Groups I–III of the Periodic Table, (for example, an aluminum alkyl), and a compound of a transition metal of Groups IV–VIII of the Periodic Table, (for example, a titanium halide). A typical crystallinity is about 60% as measured by X-ray diffraction. As used herein, semi-crystalline means a crystallinity of at least about 5–10% as measured by X-ray diffraction. Also, the typical weight average molecular weight (Mw) of the normally solid polypropylene of commerce is 100,000–4,000,000, while the typical number average molecular weight (Mn) thereof is 40,000–100,000. Moreover, the melting point of the normally solid polypropylene of commerce is from about 159°–169° C. for example 162° C. Also available commercially and useful herein is syndiotactic polypropylene.

As used herein, the general term "propylene polymer material" means: (I) isotactic or syndiotactic polypropylene and blends thereof; (II) crystalline and semi-crystalline random copolymers and terpolymers comprising a majority of propylene and at least one comonomer selected from the group consisting of ethylene and $C_4$–$C_8$ alpha-monoolefins, and mixtures of said copolymers and terpolymers with themselves and one another; particularly a polymer selected from the group consisting of (a) random crystalline propylene terpolymers consisting essentially of from about 85–96%, preferably about 90–95%, more preferably about 92–94% propylene, and from about 1.5–5.0%, preferably about 2–3%, more preferably about 2.2–2.7% ethylene and from about 2.5– 10.0%, preferably about 4–6%,, more preferably about 4.5–5.6% of an olefin selected from the group consisting of $C_4$–$C_8$ alpha-olefins, wherein the total comonomer concentration with propylene is from about 4.0 to about 15.0% (mixtures of such terpolymers can be used); (b) compositions of random crystalline propylene polymers comprising: (1) 30–65%, preferably 35–65%, more preferably 45–65% of a copolymer of from about 80%–98%, preferably about 85–95% propylene with a $C_4$–$C_8$ alpha-olefin; and (2) 35–70%, preferably 35–65%, more preferably 35–55% of a copolymer of propylene and ethylene and optionally from about 2–10%, preferably 3–6% of a $C_4$–$C_8$ alpha-olefin, said copolymer containing 2–10% ethylene, preferably 7–9% when said $C_4$–$C_8$ alpha-olefin is not present and 0.5–5%, preferably 1–3% when said $C_4$–$C_8$ alpha-olefin is present (mixtures of such copolymers can be used); (c) compositions of crystalline propylene polymers in combination with a predominantly ethylene copolymer consisting essentially of: (1) about 15–35%, preferably 17–33%, more preferably 20–30% of a terpolymer of from about 90–93%, preferably about 91–93% propylene and about 2–3.5%, preferably about 2.2–3.2% ethylene and about 5–6%, preferably 5.5–6.5% $C_4$–$C_8$ alpha-olefin (and mixtures of such terpolymers); and (2) about 30–75%, preferably 34–70%, more preferably 40–60% of a copolymer of from about 80–90%, preferably about 85–95% propylene with a $C_4$–$C_8$ alpha-olefin (and mixtures of such copolymers); and (3) about 20–60%, preferably 25–58%, more preferably 30–50% of a copolymer of from about 91–95%, preferably 92–94% ethylene with a $C_4$–$C_8$ alpha-olefin (and mixtures of such copolymers); and (d) compositions of random crystalline propylene polymer comprising from about 1.5 to about 20.0 weight percent ethylene or a $C_4$–$C_8$ alpha-olefin, preferably about 3.0 to about 18.0 percent, more preferably for ethylene about 4.0 to about 8.0 percent and for a $C_4$–$C_8$ alpha-olefin about 8.0 to about 16.0 percent; when an alpha-olefin other than ethylene is used, it is preferably butene-1. Component (c) (3) is known in the art as linear low density polyethylene. Composition (c) also can be prepared by blending, after polymerization, component (c) (3) with polymerized composition comprising components (c) (1) and (c) (2) are preferably components (a), (b) and (c) are prepared by direct polymerization.

Also, "propylene polymer material" means (III) heterophasic polyolefin compositions obtained by sequential copolymerization or mechanical blending, comprising: a) homopolymers of propylene, or its crystalline copolymers with ethylene and/or other α-olefins, and b) an ethylene-propylene elastomeric copolymer fraction. Heterophasic polyolefin compositions of this type are included, for example, among those described in European patent application EP 1-14 416 379, and in European patent EP B-77 532. Incorporation of the sorbitol derivatives of the instant invention in heterophasic compositions would not be expected to provide improved clarity and would ordinarily not be used for that purpose. However, such derivatives would be useful to modify the crystallization response of such polymers since the derivatives function as nucleators in each of the polymer compositions useful herein.

Heterophasic polyolefin compositions identified as (III), above, comprise (by weight):

a) 90–55 parts, preferably 60–80, of polypropylene homopolymer having an isotactic index greater than 90, and/or a crystalline copolymer of propylene with ethylene and/or with an e-olefin of formula $CH_2$=CHR, where R is a $C_2$–$C_6$ alkyl radical, containing less than 10% of ethylene and/or α-olefin, preferably from 0.5 to 9%, more preferably from 2 to 6% by weight, and b) 10–45 parts, preferably 20–40, of an elastomeric copolymer of propylene with ethylene and/or with an α-olefin of formula $CH_2$=CHR, where R is a $C_2$–$C_6$ alkyl radical, containing from 50 to 70 parts by weight of comonomers, and from 10 to 40% by weight of a portion insoluble in xylene at ambient temperature.

The $C_4$–$C_8$ alpha-olefin is selected from the group consisting of linear and branched alpha-olefins such as, for example, 1-butene; isobutylene; 1-pentene; 1-hexene; 1-octene; 3-methyl-1-butene; 4-methyl-1-pentene; 3,4-dimethyl-1-butene; 3-methyl-1-hexene and the like. Particularly preferred is 1-butene.

Heterophasic polymer compositions are available commercially (HIMONT U.S.A., Inc.). They can be prepared by way of sequential polymerization, where the individual components are produced in each one of sequential stages; for example, one can polymerize propylene in the first stage, optionally with minor quantities of ethylene and/or an α-olefin to form component (a), and in the second stage one can polymerize the blends of propylene with ethylene and/or with an α-olefin to form elastomeric component (b). In each stage one operates in the presence of the polymer obtained and the catalyst used in the preceding stage.

The operation can take place in liquid phase, gas phase, or liquid-gas phase. The temperature in the various stages of polymerization can be equal or different, and generally ranges from 20° C. to 100° C. As molecular weight regulators one can use the traditional chain transfer agents known in the art, such as hydrogen and ZnEt2.

The sequential polymerization stages take place in the presence of stereospecific Ziegler-Natta catalysts. Such catalysts contain, as essential elements, an Al-alkyl compound and a solid catalyst component comprising a titanium compound having at least one titanium-halide bond and an electron-donor compound which are supported on magnesium halide in active form. Catalysts having these characteristics are well known in patent literature. The catalysts described in U.S. Pat. No. 4,339,054 and EP patent 45 977 have proven to be particularly suitable. Other examples of catalysts are described in U.S. Pat. Nos. 4,472,524, and 4,473,660.

Other useful polyolefins include linear low density polyethylene (LLDPE), low-density polyethylene (LDPE), medium density polyethylene, high-density polyethylene (HDPE), polymethylpentene and mixtures of at least two of these, including the propylene polymers described above. Preferred polyolefin resins are the propylene homopolymer, propylene/ethylene copolymer, linear low density polyethylene and low-density polyethylene. Propylene polymers having a significant proportion by weight of propylene units are especially preferred.

Examples of the sorbitol derivative of the present invention include:
1,3-(4-tolylidene)-2,4-(2-thiophenylidene)-D-sorbitol;
1,3-(p-methylthiobenzylidene)-2,4-(p-tolylidene)-D-sorbitol;
1,3-(p-n-butylbenzylidene)-2,4-(p-tolylidene)-D-sorbitol;
1,3-2,4-di-(4-n-butylbenzylidene)-D-sorbitol; and
1,3-2,4-di-(2-naphthylidene)-D-sorbitol.

Useful compositions are also obtained with mixtures of the sorbitol derivatives of this invention and 1,3-2,4-di- (4 -tolylidene)-D-sorbitol, wherein the latter compound is present in the mixture at a concentration of from about 5 to about 50% by weight. The mixture, particularly when $R^1$ is

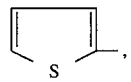

R is

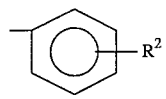

and $R^2$ is methyl [particularly 1,3-(4 -tolylidene)-2,4-(2-thiophenylidene)-D-sorbitol] provides a synergistic additive composition which produces clarity exceeding that expected from a linear mixture of the individual additive elements. Furthermore, a mixture of 1,3 -2,4-di-(2-naphthylidene)-D-sorbitol and 1,3-2,4-5,6-tri-(2 -naphthylidene)-D-sorbitol, in a weight ratio of from about 1:5 to about 5:1, for example in a 3:2 mixture by weight, also provides useful results.

The amount of the sorbitol derivative to be incorporated in the polyolefin composition of this invention is from about 0.005 to about 2% by weight, preferably from about 0.05 to about 1% by weight, especially preferably from about 0.1 to about 0.7% by weight, based on the weight of the composition.

The sorbitol derivative of this invention can be obtained by using and reacting D-sorbitol as a basic building block to obtain the desired final product. A generalized synthesis scheme is as follows: D-sorbitol is reacted with the desired aldehyde or corresponding acetal in water at 0°–25° C. in the presence of hydrochloric acid. Theoretically the reaction is reversible so that isolation of the product is dependent on its solubility in water. If the compound is sufficiently insoluble in water at 0°–25° C. it precipitates out of the reaction mixture before hydrolyzing back to the starting materials.

The composition of this invention can be obtained by adding a predetermined amount of the dibenzylidene sorbitol derivative to the polyolefin resin and mixing them by any desired mixing means, e.g., a Banbury brand internal mixer or mixing extruder. Mixing conditions are within the skill of those familiar with the art of preparing polyolefin compositions comprising additives which are required to be uniformly dispersed in the polyolefin.

The composition of this invention may also include other additives such as stabilizers, antioxidants, antislip agents, flame retardants, lubricants, fillers, coloring agents, antistatic and antisoiling agents, and the like, so long as these additives do not adversely affect the improved transparency and nucleation response of the composition of this invention.

The expression "consisting essentially of" as used in this specification excludes an unrecited substance at a concentration sufficient to materially adversely affect the basic and novel characteristics of the claimed invention.

The following examples are provided to illustrate, but not limit, the invention disclosed and claimed herein. Transparency or haze was determined in accordance with ASTM D1003A-61A. The random propylene copolymer referred to in the examples was an ethylene copolymer, containing 3.3–3.5 weight % ethylene and having a 12 Melt Flow Rate. It was free of stabilizers and other additives which might otherwise be present in a commercial product since it was intended that stabilizers and additives would be added to the copolymer. Sample preparation was generally as follows: the polymer resin (in spherical particle form) was dry blended at room temperature with the D-sorbitol derivative and a stabilization package which included calcium stearate, Irganox 1010 and Irganox 168 (Ciba-Geigy Corporation); the composition was extruded in a single screw extruder at 230° C.; test plaques were injection molded (3 in.×3 in.×40 mils) at 218° C.

EXAMPLE 1

D-sorbitol was reacted with 2-thiophenecarboxaldehyde in water at 0°–25° C. in the presence of hydrochloric acid to produce 2,4-(2-thiophenylidene)-D-sorbitol. This intermediate product was tested in a comparative test for its ability to clarify a random propylene copolymer at a concentration of 0.25% in comparison to a commercial clarifier, Millad 3905 (1,3-2,4-di-(benzylidene)-D-sorbitol, Milliken Chemical Company). The composition containing Millad 3905 had a % haze value of 21.9, whereas a composition containing the intermediate product had a value of 54.1.

2,4-(2-thiophenylidene)-D-sorbitol was reacted with p-tolualdehyde in refluxing cyclohexane-dimethylsulfoxide mixture using p-toluenesulfonic acid as a catalyst under nitrogen. The water eliminated from the reaction was separated using a Dean Stark apparatus. The product, 1,3-(4 -tolylidene)-2,4-(2-thiophenylidene)-D-sorbitol was isolated as a 3:1 mixture with 1,3–2,4-di-(4-tolylidene)-D-sorbitol (available commercially as Millad 3940, Milliken Chemical Company). The 3:1 mixture was tested for clarifying properties at a concentration of 0.25% in a random propylene copolymer and compared to each of the commercially available materials with the following results:

| Material | Haze (%) |
|---|---|
| Millad 3905 | 18.9 |
| Millad 3940 | 9.6 |
| Example 1 (3:1 Mixture) | 12.5 |

Additional comparative tests were conducted to determine the effect of the presence of Millad 3940 in the Example 1 product mixture. Use of 0.05% (the approximate concentration in a 3:1 mixture=¼ of the total concentration of 0.25% of the additive used in the tests) of Millad 3940 alone resulted in a haze value of 48.6%; in the absence of a clarifier the haze value was 52%. At a minimum, this demonstrates a synergistic effect for the presence of the additive of the present invention in the mixture.

EXAMPLE 2

D-sorbitol was reacted with 4-tolualdehyde in water at 0°–25° C. in the presence of hydrochloric acid to produce 2,4-(p-tolylidene)-D-sorbitol. As described in Example 1, this intermediate product was tested in a comparative test for its ability to clarify a random propylene copolymer at a concentration of 0.25% in comparison to the commercial clarifier, Millad 3905. The composition containing Millad 3905 had a % haze value of 21.9, whereas a composition containing the intermediate product had a value of 36.3.

2,4-(p-tolylidene)-D-sorbitol was reacted in one instance (A) with 4-methylthiobenzaldehyde and in the other with (B) 4-n-butylbenzylaldehyde diethylacetal in refluxing cyclohexanedimethylsulfoxide mixture in the presence of a catalytic amount of p-toluenesulfonic acid under nitrogen. The resulting products were (A) 1,3-(p-methylthiobenzylidene)-2,4-(p-tolylidene)-D-sorbitol and (B) 1,3-(p-n-butylbenzylidene)-2,4-(p-tolylidene)-D-sorbitol. Compound (A) was tested as in Example 1 (at a concentration of 0.25%) with a resulting haze value of 20.6%.

EXAMPLE 3

D-sorbitol was reacted with 4-n-butylbenzaldehyde diethyl acetal and 2-naphthaldehyde in refluxing cyclohexanedimethylsulfoxide mixture in the presence of a catalytic amount of p-toluenesulfonic acid under nitrogen. For comparative purposes, the intermediate D-sorbitol based on 4-n-butylbenzaldehyde resulted in a haze level of 34.1% when tested as described in Example 1. The further reaction products of this example were (A) 1,3-2,4-di-(4-n-butylbenzylidene)-D-sorbitol and (B) 1,3-2,4-di-(2-naphthylidene)-D-sorbitol. Compound B was not isolated in pure form, but was in a 3:2 mixture with what was believed to be 1,3-2,4-5,6-tri-(2-naphthylidene)-D-sorbitol. Compounds 3A and 3B were tested in random propylene copolymer for clarity at a concentration of 0.25%; the resulting haze values were 17.9 and 20.1%.

What is claimed is:
1. A polyolefin composition consisting essentially of at least semi-crystalline to crystalline one homopolymer or copolymer of a $C_2$ to $C_8$ alpha-monoolefin and about 0.05 to about 2.5% by weight, of said composition of a D-sorbitol derivative of the following formula:

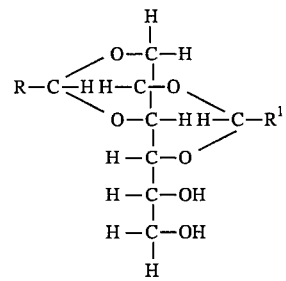

wherein:
(a) R and $R^1$ are the same and represent a member selected from the group consisting of

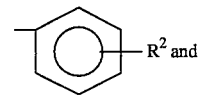

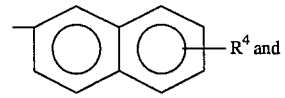

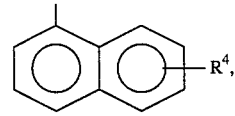

wherein $R^2$ is mono-, di- or tri-substituted on the ring and represents a member selected from the class consisting of $NO_2$ and CN; and wherein $R^4$ is mono-, di-, or tri-substituted on the ring and represents a member selected from the class consisting of $C_1$–$C_6$ alkyl or O-alkyl, and $NO_2$; or (b) R and $R^1$ are different and one of R and $R^1$ is

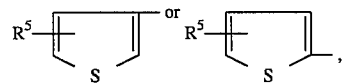

wherein $R^5$ represents a member selected from the class consisting of H, $C_1$–$C_6$ alkyl, $NO_2$, Cl, Br and F, and the other of R and $R^1$ is

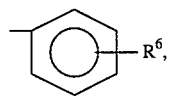

wherein $R^6$ is mono-, di-, or tri-substituted on the ring and represents a member selected from the class consisting of alkyl or O-alkyl groups having 1 to 8 carbon atoms, $NO_2$, CN and COOY, wherein Y is an alkyl having 1 to 8 carbon atoms; or (c) R and $R^1$ are different and R is

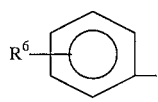

wherein $R^6$ is as defined above, and $R^1$ is

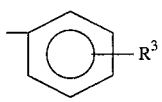

wherein $R^3$ is mono-, di-, or tri-substituted on the ring and represents an alkyl group having 4 to 6 carbon atoms.

2. The composition of claim 1 wherein said $C_2$ to $C_8$ alpha-monoolefin is selected from the group consisting of ethylene, propylene, butene-1 and 4-methylpentene.

3. The composition of claim 1 wherein said polyolefin is selected from the group consisting of polyethylene and propylene polymer material.

4. The composition of claim 3 wherein said propylene polymer material is selected from the group consisting of polypropylene homopolymer, propylene-ethylene copolymers, propylene-butene-1 copolymers, and propylene-ethylene-butene-1 terpolymers.

5. The composition of claim 1 wherein $R^1$ is

R is

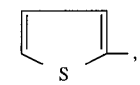

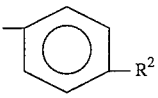

and $R^2$ is methyl.

6. The composition of claim 5, which also comprises 1,3 -2,4-di-(4-tolylidene)-D-sorbitol.

7. The composition of claim 1 wherein R is

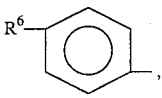

is methyl, $R^1$ is

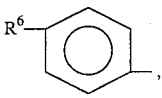

and $R^3$ is n-$C_4H_9$.

* * * * *

UNITED STATES PATENT AND TRADEMARK OFFICE
CERTIFICATE OF CORRECTION

PATENT NO. : 5,470,898
DATED : November 28, 1995
INVENTOR(S) : Abuzar Syed

It is certified that error appears in the above-indentified patent and that said Letters Patent is hereby corrected as shown below:

At col. 12, line 24, insert --$R^6$-- before "is methyl".

Signed and Sealed this

Sixteenth Day of July, 1996

Attest:

BRUCE LEHMAN

*Attesting Officer*    *Commissioner of Patents and Trademarks*